United States Patent [19]
Lash et al.

[11] Patent Number: 4,935,022
[45] Date of Patent: Jun. 19, 1990

[54] THIN ABSORBENT ARTICLES CONTAINING GELLING AGENT

[75] Inventors: Glen R. Lash, Cincinnati; Leonard R. Thompson, Fairfield, both of Ohio

[73] Assignee: The Procter & Gamble Company, Cincinnati, Ohio

[21] Appl. No.: 154,825

[22] Filed: Feb. 11, 1988

[51] Int. Cl.$^5$ ............................................. A61F 13/16
[52] U.S. Cl. .................................. 604/368; 604/375
[58] Field of Search ............... 604/368, 374, 375, 378, 604/385.1

[56] References Cited

U.S. PATENT DOCUMENTS

| | | | |
|---|---|---|---|
| 3,224,926 | 12/1965 | Bernardin | 162/146 |
| 3,241,553 | 3/1966 | Steiger | 128/156 |
| 3,440,135 | 4/1969 | Chung | 162/157 |
| 3,658,613 | 4/1972 | Steiger | 156/153 |
| 3,683,916 | 8/1972 | Mesek et al. | 128/287 |
| 3,763,863 | 10/1973 | Mesek et al. | 128/287 |
| 3,932,209 | 1/1976 | Chatterjee | 162/157 C |
| 3,938,522 | 2/1976 | Repke | 128/287 |
| 4,035,147 | 7/1977 | Sangenis et al. | 8/116.4 |
| 4,102,340 | 7/1978 | Mesek et al. | 128/287 |
| 4,217,901 | 8/1980 | Bradstreet et al. | 128/290 R |
| 4,259,958 | 4/1981 | Goodbar | 128/287 |
| 4,381,782 | 5/1983 | Mazurak et al. | 604/368 |
| 4,500,315 | 2/1985 | Pieniak et al. | 604/379 |
| 4,573,989 | 3/1986 | Karami et al. | 604/381 |
| 4,610,678 | 9/1986 | Weisman et al. | 604/368 |
| 4,654,039 | 5/1987 | Brandt et al. | 604/368 |
| 4,673,402 | 6/1987 | Weisman et al. | 604/368 |
| 4,685,909 | 8/1987 | Berg et al. | 604/375 |
| 4,699,619 | 10/1987 | Bernardin | 604/378 |
| 4,699,823 | 10/1987 | Kellenberger et al. | 428/219 |
| 4,822,453 | 4/1989 | Dean et al. | 604/375 |

FOREIGN PATENT DOCUMENTS

| | | |
|---|---|---|
| 158914 | 10/1985 | European Pat. Off. . |
| 251675 | 1/1988 | European Pat. Off. . |
| 252650 | 1/1988 | European Pat. Off. . |
| 59-188418 | 12/1984 | Japan . |
| 2063683 | 1/1981 | United Kingdom . |

OTHER PUBLICATIONS

Sanyo Chem. Ind.; "Superabsorbent Polymer—SANWET IM-300/SANWET IM-1000"; Oct. 1982.
Nippon Shokubai Kagaku Kogyo K.K.; "Aqualic CA"; undated.
Stockhausen Inc.; "Favor SAB-901"; Jul. 1983.
BASF AG; "Luquasorb HC 9780—Superasorent Based on Polyacrylic Acid for Aqueous Fluids"; undated.

Primary Examiner—C. Fred Rosenbaum
Assistant Examiner—Sharon Rose
Attorney, Agent, or Firm—George W. Allen; Jerry J. Yetter; Richard C. Witte

[57] ABSTRACT

The present invention provides absorbent articles, such as disposable diapers, which utilize a particular type of stiffened cellulose fibers and a particlar type and form of polymeric gelling agent particles to enhance the absorbency characteristics of such articles. In these articles, the gelling agent material, combined in particulate form of a certain size with stiffened cellulose fiber material, is primarily placed in a lower fluid storage layer of the absorbent core of the article. Such a fluid storage lower layer of the absorbent core is placed underneath an upper, generally larger, fluid acquisition/distribution layer which also contains stiffened cellulose fibers and gelling agent particles of a certain size. This lower fluid storage layer is generally positioned toward the front of the absorbent article. Absorbent articles of this type can be fashioned into especially thin, compact, nonbulky diapers.

20 Claims, 1 Drawing Sheet

THIN ABSORBENT ARTICLES CONTAINING GELLING AGENT

BACKGROUND OF THE INVENTION

This invention relates to absorbent articles using both cellulosic fiber material and particles of a hydrogel-forming polymeric gelling agent as absorbents. Absorbent articles of this type include disposable diapers, adult incontinence pads and briefs and the like which are required to handle relatively large amounts of discharged body fluids.

Absorbent structures which comprise entangled masses of fibers, i.e., fibrous webs, are well known in the art. Such structures can imbibe liquids, such as discharged body fluids, both by an absorption mechanism wherein fluid is taken up by the fiber material itself and by a wicking mechanism wherein fluid is acquired by, distributed through and stored in the capillary interstices between fibers. One means for improving the absorbency characteristics of such fibrous web structures is to incorporate therein so-called superabsorbent polymers which imbibe fluid to thereby form a swollen hydrogel material. The resulting hydrogel serves to retain fluid such as discharged body liquids within the structure. An absorbent structure of this type wherein hydrogel-forming materials in particulate form are incorporated into fibrous webs is disclosed in Weisman and Goldman; U.S. Pat. No. 4,610,678; issued Sept. 9, 1986.

The improvement in absorbency provided by incorporation of hydrogel-forming absorbent gelling materials has permitted the realization of absorbent articles such as diapers which employ relatively thin absorbent cores and which are, therefore, relatively thin products. Thinner diapers are less bulky to wear and fit better under clothing. They are also more compact in the package, making the diapers easier for the consumer to carry and store. Compactness in packaging also results in reduced distribution costs for the manufacturer and distributor.

In order to realize acceptable thin absorbent articles which retain desirable absorbency characteristics, it is essential that the absorbent core of such articles be of a configuration which tends to maximize the absorbent efficiency of both the fibrous matrix and the polymeric gelling agent material, if any, used therein. One such absorbent core configuration is disclosed in Weisman/Houghton/Gellert; U.S. Pat. No. 4,673,402; issued June 16, 1987. This patent discloses absorbent articles having a dual layer absorbent core. In the dual layer configuration, the core comprises an upper primary layer which is an airlaid web of hydrophilic fiber material, optionally with a small amount of polymeric gelling agent particles admixed therewith. The core also comprises an underlying insert layer which is an airlaid mixture of hydrophilic fiber material and a substantial amount of polymeric gelling agent particles. This insert layer is generally positioned toward the front of the absorbent article such that more than half of the polymeric gelling agent material in the article is found in the front half thereof. Absorbent articles having the particular dual layer configuration of the '402 patent can be prepared in the form of especially thin, highly effective, low leakage diaper products.

Notwithstanding the existence of thin absorbent articles of the type described in the '402 patent, there is a continuing need to identify preferred configurations for absorbent articles which would permit the realization of even thinner products employing less absorbent material therein. Such articles would be even less costly to manufacture and distribute than existing known products. Such products would also find great acceptance among consumers looking for especially thin, better fitting, low leakage products.

Accordingly, it is an object of the present invention to provide improved absorbent articles utilizing a dual layer absorbent core that effectively and efficiently absorbs and stores the wearer's discharged body fluids.

It is a further object of the present invention to provide such improved absorbent articles in the form of very thin, easy to manufacture, compact products using less absorbent material than similar products of the prior art.

It is a further object of the present invention to provide such thin, compact, nonbulky absorbent articles having leakage incidence which is equivalent to or lower than that of existing commercially marketed disposable absorbent products.

SUMMARY OF THE INVENTION

The present invention provides an especially thin absorbent article such as a diaper or incontinence brief or pad which is suitable for absorbing body fluids in an especially effective and efficient manner. Such an absorbent article comprises an elongated liquid impervious backing sheet, a liquid previous topsheet and a layered, absorbent core positioned between the backing sheet and the topsheet.

The absorbent core comprises both an upper fluid acquisition/distribution layer which is preferably elongated and a lower fluid storage layer. Both layers comprise combinations of stiffened, twisted, curled cellulose fibers and particles of a hydrogel-forming polymeric gelling agent thoroughly dispersed among such fibers.

The upper fluid acquisition layer has a density of from about 0.05 to 0.25 g/cm$^3$, a basis weight of from about 0.01 to 0.10 g/cm$^2$ and comprises from about 3% to 15% by weight of the upper layer of particles of the polymeric gelling agent. The lower fluid storage layer has a density of from about 0.06 to 0.3 g/cm$^3$, a basis weight of from about 0.02 to 0.12 g/cm$^2$ and comprises from about 15% to 60% by weight of the lower layer of the polymeric gelling agent particles.

In both upper and lower layers, the hydrogel-forming polymeric gelling agent has an equilibrium gel volume of at least about 20 grams of synthetic urine per gram of gelling agent. In the upper layer, such gelling agent particles also have a mass median particle size ranging from about 400 to 1680 microns. Preferably no more than about 16% by weight of these upper layer particles have a particle size less than 200 microns and no more than about 16% by weight of these upper layer particles have a particle size greater than 1410 microns.

The lower fluid storage layer of the absorbent core has a top surface area which is from about 0.25 to 0.95 times the top surface area of the upper fluid acquisition/distribution layer. The lower fluid storage layer is further positioned relative to the upper fluid acquisition/distribution layer in a manner such that at least about 75% of the gelling agent material in the lower layer is found within the front two-thirds section of the article and such that at least about 55% of the total gelling agent material in the lower layer is found within the front half section of the article.

Preferably the stiffened, twisted, curled cellulose fibers used in both layers are cellulose fibers which have been internally crosslinked with a monomeric crosslinking agent. Such fibers preferably have an average dry fiber twist count of at least about 4.5 twist nodes per millimeter, an average wet fiber twist count of at least 3.0 twist nodes per millimeter, and an average wet fiber twist count of at least about 0.5 twist nodes per millimeter less than the average dry fiber twist count. Furthermore, such fibers will preferably have a curl factor of at least about 0.30, a water retention value (WRV) of from about 28% to 50% and an alcohol retention value (ARV) of less than about 30%.

DETAILED DESCRIPTION OF THE INVENTION

The absorbent articles of the present invention can be manufactured in the configuration of wearable disposable products which are capable of absorbing significant quantities of water and body waste fluids such as urine and feces. Thus such articles, for example, may be prepared in the form of disposable diapers, adult incontinence briefs, adult incontinence pads and the like.

The absorbent articles herein generally comprise three basic structural components. One such component is an elongated, liquid impervious backing sheet. On top of this backing sheet is placed an absorbent core which itself comprises two or more distinct layers. On top of this absorbent core is placed a water previous topsheet. The topsheet is the element of the article which is placed next to the skin of the wearer.

Especially preferred absorbent articles of this invention are disposable diapers. Articles in the form of disposable diapers are fully described in Duncan and Baker, U.S. Pat. Re. No. 26,151, Issued Jan. 31, 1967; Duncan, U.S. Pat. No. 3,592,194, issued July 13, 1971; Duncan and Gellert, U.S. Pat. No. 3,489,148, issued Jan. 13, 1970; Buell, U.S. Pat. No. 3,860,003, issued Jan. 14, 1975; Weisman and Goldman, U.S. Pat. No. 4,610,678, issued Sept. 9, 1986 and Weisman, Houghton and Gellert; U.S. Pat. No. 4,673,402; issued June 16, 1987, which patents are incorporated herein by reference. A preferred disposable diaper for the purpose of this invention comprises an absorbent core; a topsheet superposed or co-extensive with one face of the core, and a liquid impervious backsheet superposed or co-extensive with the face of the core opposite the face covered by the topsheet. Both the backsheet and the topsheet most preferably have a width greater than that of the core thereby providing side marginal portions of the backsheet and topsheet which extend beyond the core. Frequently the backsheet and the topsheet will be fused together in these side marginal portions. The diaper is preferably constructed in an hourglass configuration.

The backsheet of the articles herein can be constructed, for example, from a thin, plastic film of polyethylene, polypropylene, or other flexible moisture impeding material which is substantially water impervious. Polyethylene, having an embossed caliper of approximately 1.5 mils, is especially preferred.

The topsheet of the article herein can be made in part or completely of synthetic fibers or films comprising such materials as polyester, polyolefin, rayon, or the like, or of natural fibers such as cotton. In nonwoven topsheets, the fibers are typically bound together by a thermal binding procedure or by a polymeric binder such as polyacrylate. This sheet is substantially porous and permits a fluid to readily pass therethrough into the underlying absorbent core.

Another suitable type of topsheet comprises the topsheets formed from liquid impervious polymeric material such as polyolefins. Such topsheets can have tapered capillaries of certain diameter and taper positioned in the topsheet to permit flow of discharged fluid through the topsheet into the underlying absorbent core of the article.

All of the topsheets used in the articles of the present invention are relatively hydrophobic in comparison with the absorbent core of said articles. Topsheet construction is generally disclosed in Davidson, U.S. Pat. No. 2,905,176, issued Sept. 22, 1959; Del Guercio, U.S. Pat. No. 3,063,452, issued Nov. 13, 1962; Holliday, U.S. Pat. No. 3,113,570, issued Dec. 10, 1963, and Thompson, U.S. Pat. No. 3,929,135; issued Dec. 30, 1975; which patents are incorporated herein by reference. Preferred topsheets are constructed from polyester, rayon, rayon/polyester blends, polyethylene or polypropylene.

An absorbent core, which itself comprises two or more distinct layers, and which is preferably flexible, is positioned between the elongated backing sheet and the topsheet to form the absorbent articles herein. This core essentially comprises both an upper fluid acquisition/distribution layer and a lower fluid storage layer. It should be understood that for purposes of this invention these two types of layers refer merely to the upper and lower zones of the absorbent core and are not necessarily limited to single layers or sheets of material. Thus both the fluid acquisition/distribution layer and the fluid storage layer may actually comprise laminates or combinations of several sheets or webs of the requisite type of materials as hereinafter described. Thus as used herein, the term "layer" includes the terms "layers" and "layered." For purposes of this invention, it should also be understood that the term "upper" refers to the layer of the absorbent core which is nearest to the article topsheet; conversely, the term "lower" refers to the layer of the absorbent core which is nearest the article backing sheet.

One essential element of the absorbent core is an upper fluid acquisition/distribution layer which comprises a combination of a particular type of hydrophilic cellulosic fiber material, defined more fully hereinafter, and particles of a certain type of polymeric gelling agent also defined more fully hereinafter. This fluid acquisition/distribution layer serves to quickly collect and temporarily hold discharged body fluid. Since such fluid is discharged in gushes, the upper acquisition/distribution layer must be able to quickly acquire and transport fluid by wicking from the point of initial fluid contact to other parts of the acquisition/distribution layer. In the context of the present invention, it should be noted that the term "fluid" means "liquid."

The principal function of the upper layer of the absorbent core is to receive fluids passing through the water previous topsheet and to transport such fluids to other areas of the upper layer and eventually on to the fluid-holding, gelling agent-containing lower fluid storage layer of the core. The upper layer can, however, function as a storage zone for a small amount of fluid and, for this reason, will essentially contain a small amount of hydrogel-forming polymeric gelling agent in particulate form. Gelling agent particles of the type hereinafter defined will thus comprise from about 3% to 15% by weight, more preferably from about 5% to 8% by weight, of the upper layer of the absorbent core. The gelling agent used in the upper layer does not have to be identical to the gelling agent essentially employed in the lower layer so long as it is of the general type of gelling agent hereinafter defined.

The shape, size and character, including capillarity (e.g., density), of the upper fluid acquisition/distribution layer of the articles herein is of some importance in determining the effectiveness of the resulting absorbent articles in absorbing discharged body fluids. As indicated, the upper absorbent layer of the core is preferably elongated. For purposes of this invention, this means that the upper layer, like the backing sheet, is elongated if it is of unequal length and width in the unfolded, flat configuration. The upper layer in the unfolded configuration can be of any desired shape, for example, rectangular, trapezoidal, oval, oblong or hourglass-shaped. The shape of the upper fluid acquisition/distribution layer of the core will frequently define the general shape of the resulting absorbent article.

The upper fluid acquisition/distribution layer will generally have a density of from about 0.05 to 0.25 g/cm$^3$. The basis weight of the upper layer of the absorbent core will typically range from about 0.01 to 0.10 g/cm$^2$. In preferred embodiments of the present invention the upper fluid acquisition/distribution layer of the core will be hourglass-shaped and will have a density within the range of from about 0.07 to 0.14 g/cm$^3$, more preferably from about 0.07 to 0.12 g/cm$^3$. In such preferred embodiments, the upper fluid acquisition/distribution layer of the core will also have a basis weight ranging from about 0.010 to 0.025 g/cm$^2$, more preferably from about 0.013 to 0.020 g/cm$^2$. Density and basis weight need not be uniform throughout the upper layer. Within the foregoing ranges, the upper layer can contain regions of relatively higher or relatively lower density and basis weight. Density values are calculated from basis weight and layer caliper. Caliper is measured under a confining pressure of 0.176 psi (1.26 kPa). Density and basis weight values include the weight of the gelling agent particles.

A second essential element of the absorbent core is a lower fluid storage layer which, like the upper layer, comprises a combination of a particular type of hydrophilic cellulosic fiber material, defined more fully hereinafter, and particles of a certain type of polymeric gelling agent also defined more fully hereinafter. The principal function of the fluid storage layer is to absorb discharged body fluid from the upper acquisition/ distribution layer and retain such fluid under the pressures encountered as a result of the wearer's movements. Ideally the fluid storage lower layer will drain the upper layer of much of its acquired fluid load.

In general, the lower fluid storage layer will contain a higher concentration of the gelling agent particles than does the upper layer. The relative amount of hydrophilic cellulosic fiber material and gelling agent particles used in the lower fluid storage layer of the articles herein can be most conveniently expressed in terms of a weight percentage of the gelling agent in the lower layer. The lower fluid storage layer of the absorbent cores herein must contain from about 15% to 60%, preferably from about 20% to 50%, by weight of the lower layer of gelling agent material.

The density of the lower fluid storage layer of the absorbent core can be of some importance in determining the absorbent properties of the resulting absorbent article. The density of the lower fluid storage layer will generally be in the range of from about 0.06 to about 0.3 g/cm$^3$, and more preferably within the range of from about 0.09 to about 0.25 g/cm$^3$, most preferably from about 0.15 to 0.20 g/cm$^3$. Typically the basis weight of the lower fluid storage layer can range from about 0.02 to 0.12 g/cm$^2$, more preferably from about 0.04 to 0.08 g/cm$^2$, most preferably from about 0.05 to 0.07 g/cm$^2$.

As with the upper layer, density and basis weight need not be uniform throughout the lower layer. Within the foregoing ranges, the lower layer can contain regions of relatively higher and relatively lower density and basis weight. Also as with the upper layer, density values for the lower layer are calculated from basis weight and layer caliper measured under a confining pressure of 0.176 psi (1.26 kPa). Density and basis weight values include the weight of the gelling agent particles.

Both layers of the absorbent core of the absorbent articles herein essentially comprise stiffened, twisted, curled cellulose fibers. Such fibers are cellulosic fibers such as wood pulp fibers which have been internally crosslinked with monomeric crosslinking agents preferably while such fibers are in a relatively dehydrated, defibrated, twisted, curled condition. The effect of crosslinking under these conditions is to form fibers which are stiffened and which tend to retain their twisted, curled configuration during use in the absorbent articles herein.

Stiffened, twisted, curled cellulose fibers which are internally crosslinked, as well as processes for their preparation, are well known in the art. Fibers of this general type are disclosed, for example, in Bernardin, U.S. Pat. No. 3,224,926, issued Dec. 21, 1965; Steiger, U.S. Pat. No. 3,241,553, issued Mar. 22, 1966; Chung, U.S. Pat. No. 3,440,135, issued Apr. 22, 1969, Steiger, U.S. Pat. No. 3,658,613, issued Apr. 25, 1972; Chatterjee, U.S. Pat. No. 3,932,209, issued Jan. 13, 1976 and Sangenis et al, U.S. Pat. No. 4,035,147, issued July 12, 1977. All of these patents are incorporated herein by reference. The crosslinked cellulose fibers disclosed in these patents are all useful as the stiffened, twisted, curled cellulose fiber component of both absorbent core layers of the articles herein.

The extent to which the stiffened fibers useful in the absorbent core layers are twisted and curled can be quantified by referencing both a fiber "twist count" and a fiber "curl factor". As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°. The number of twist nodes in a certain length of fibers (i.e., the twist count) is directly indicative of the degree of fiber twist, which is a physical parameter of the fiber. The twist nodes and total twist count are determined by a Twist Count Image Analysis Method which is described in the Test Methods section hereinafter.

The actual twist count of any given sample of fibers will vary depending upon the type of fibers used to form the samples. The twist count of any particular type of wood pulp fiber may also vary from fiber to fiber within a single fiber type. The average twist count values which are utilized to define the stiffened, twisted, curled cellulose fibers employed herein apply regardless of the particular combination of fiber types in the mass of fibers utilized. Any mass of fibers having the average twist count values set forth hereinafter are meant to be encompassed within the definition of "twisted" fibers.

In the measurement of twist count for a given fiber mass sample, it is important that a sufficient number of fibers be examined in order to accurately represent the twist count of the sample as an average of the variable individual fiber twist levels. It is suggested that at least five (5) inches (12.7 cm) of cumulative fiber length of a representative sample of a mass of fibers be tested in order to provide a representative fiber twist count.

The fiber twist count described can be applied to either wet or dry fibers. The twist count determination method varies only in that the fiber is either dry or wetted with water when the twist nodes are counted in accordance with the Twist Count Image Analysis Method.

The stiffened, twisted, curled cellulose fibers essentially employed in both the upper and lower layers of the absorbent core of the articles herein will preferably have an average dry fiber twist count of at least about 4.5 twist nodes per millimeter. Furthermore, the average wet fiber twist count of these fibers should preferably be at least about 3.0 and should also preferably be at least about 0.5 twist nodes per millimeter less than the average dry fiber twist count. More preferably, the average dry fiber twist count should be at least about 5.5 twist nodes per millimeter, and the average wet fiber twist count should be at least about 4.0 twist nodes per millimeter and should also be at least 1.0 twist nodes per millimeter less than its average dry fiber twist count. Most preferably, the average dry fiber twist count should be at least about 6.5 twist nodes per millimeter, and the average wet fiber twist count should be at least about 5.0 twist nodes per millimeter and should also be at least 1.0 twist nodes per millimeter less than the average dry fiber twist count.

In addition to being twisted, the fibers essentially used in the upper and lower layers of the absorbent core are also curled. Fiber curl may be described as the fractional shortening of the fiber due to kinks, twists, and/or bends in the fiber. For the purposes of this invention, fiber curl is measured in terms of a two dimensional plane. The extent of fiber curling can be quantified by referencing a fiber curl factor. The fiber curl factor, a two dimensional measurement of curl, is determined by viewing the fiber in a two dimensional plane. To determine curl factor, the projected length of the fiber as the longest dimension of a rectangle encompassing the fiber, $L_R$, and the actual length of the fiber, $L_A$, are both measured. The fiber curl factor can then be calculated from the following equation:

Curl Factor = $(L_A/L_R) - 1$.

A Fiber Curl Factor Image Analysis Method is utilized to measure $L_R$ and $L_A$. This method is described in the Test Methods section hereinafter. Preferably the fibers utilized in the layers of the absorbent core herein will have a curl factor of at least about 0.30, and more preferably will have a curl factor of at least about 0.50.

As indicated, the twisted, curled cellulose fibers preferably used in the absorbent articles herein are those which have been stiffened by internal chemical crosslinking within the individual cellulose fiber under relatively dehydrated conditions. Such crosslinking affects both the ability of the fiber to take up fluid and the tendency of the fiber to swell. Fibers which do not swell at all in water may lack the ability to untwist upon wetting and tend to be excessively stiff. For the present invention, a certain limited amount of swelling is desired since swelling induces some useful untwisting of the fiber. Too much swelling is undesirable, however, because fibers which become highly swollen upon contact with water become too flexible to provide the desired degree of stiffness for absorbent article integrity for responsiveness to wetting and wet resilience.

Fiber stiffness as it relates to resistance to fiber wall swelling can be quantified by referencing the water retention value (WRV) of the stiffened, twisted, curled cellulose fibers used in the absorbent articles herein. WRV is a measure of the amount of water retained by a mass of fibers after substantially all of the interfiber water has been removed. A procedure for determining WRV is described in greater detail in the Test Methods section hereinafter.

The WRV for the fibers used in the present invention will preferably range between about 28% and about 50%. In more preferred embodiments, the WRV of the fibers can range from about 30% to 45%. Most preferably, the WRV ranges from about 35% to 42%. Fibers having a WRV within these ranges are believed to provide an optimal balance of swelling-induced untwisting and fiber stiffness.

Another parameter which can be used to characterize the nature of the stiffened fibers formed by crosslinking fibers in relatively dehydrated form is that of alcohol retention value (ARV). ARV is a measure of the extent to which a fluid, e.g., isopropyl alcohol, which does not induce fiber swelling, is taken up by the stiffened fibers. The ARV of the stiffened fibers is directly related to the extent that the fibers were wollen with the solution of crosslinking agent during the stiffening procedure. Relatively higher ARVs mean that the fibers were generally swollen to a relatively greater extent during crosslinking. An ARV can be determined using the procedure described in greater detail in the Test Methods section hereinafter.

Since the stiffened fibers preferably used herein are those which are crosslinked while in a relatively dehydrated state, the ARV of such fibers will generally not exceed a certain maximum value. In particular, the stiffened, twisted, curled cellulose fibers preferred for use herein are those which have an ARV of less than about 30%. The limitation that such fibers have an ARV of less than about 30% is indicative of the dehydrated, unswollen state of these fibers during the stiffening process. More preferably, the ARV of the fibers useful herein will be less than about 27%.

The stiffened, twisted, curled cellulose fibers herein having the preferred twist count, curl factor, WRV and ARV characteristics hereinbefore set forth, can be prepared by internally crosslinking such fibers in relatively dehydrated form while or after such fibers are being or have been dried and defibrated (i.e., "fluffed"). Crosslinking under these conditions enhances the amount of fiber twisting which is achieved. Thus, preferably, cellulosic fibers are stiffened and dried while in substantially individual form with fiber-to-fiber contact being minimized during drying. In general, the fibers are contacted with a crosslinking solution and subjected to one or more additional steps in which the fibers are dried and the crosslinking agent is activated. Those skilled in the art will appreciate that natural cellulosic fibers having a microfibrillar ultrastructure have a tendency to twist as they are dried of water or other fiber-swelling fluid. The degree to which a fiber will twist is dependent on a variety of factors, one of the most significant of which is the extent of fiber-to-fiber contact of the drying fibers. It is desirable to minimize fiber-to-fiber contact during drying in order to minimize interfiber hydrogen bonding of the wet or moist fibers which inhibits twisting of such fibers.

A variety of monomeric crosslinking agents including, but not limited to, $C_2$-$C_8$ dialdehydes and $C_2$-$C_8$ monoaldehydes having an acid functionality can be employed to form the crosslinking solution. These compounds are capable of reacting with at least two hydroxyl groups in a single cellulose chain or on proximately located cellulose chains in a single fiber. Crosslinking agents contemplated for use in preparing the preferred stiffened, twisted, curled cellulose fibers useful in this invention include glutaraldehyde, glyoxal, and glyoxylic acid. Glutaraldehyde is especially preferred, since it provides fibers with a high degree of absorbency and resiliency, is believed to be safe and nonirritating to human skin when crosslinked with cellulose, and provides the most stable crosslink bonds.

The crosslinking agent is generally utilized in a concentration which is sufficient to provide the requisite WRV for the fibers which are stiffened by crosslinking. Preferably, crosslinking agents of the $C_2$-$C_8$ dialdehyde type will be contacted with the cellulose fibers in a concentration ranging from about 0.75 to 2.0 mole percent calculated on a cellulose anhydroglucose molar basis. More preferably, crosslinking agent concentration will range from about 1.0 to 2.0 mole percent, and most preferably from about 1.2 to 1.6 mole percent, calculated on a cellulose anhydroglucose molar basis.

The crosslinking solution will also generally contain a catalyst. In general, any substance which catalyzes the crosslinking mechanism may be utilized. Operable catalysts include organic acids and acid salts. Especially preferred catalysts are salts such as aluminum, magnesium, zinc and calcium salts of chlorides, nitrates or sulfates. One specific example of a preferred salt of this type is zinc nitrate hexahydrate. It is believed that combinations of acid salts and organic acids as catalyzing agents provide superior crosslinking reaction efficiency. Unexpectedly high levels of reaction completion have been observed, for example, for catalyst combinations of zinc nitrate salts and organic acids, such as citric acid, and the use of such combinations is preferred.

A catalytically-effective amount of catalyst should be employed in the crosslinking solution. The amount of catalyst preferably utilized is, of course, dependent upon the particular type and amount of crosslinking agent and the reaction conditions, especially temperature and pH. In general, catalyst concentrations of between about 10 and 60 wt. %, based on the weight of crosslinking agent added to the cellulosic fibers, are useful. For exemplary purposes, in the case wherein the catalyst utilized is zinc nitrate hexahydrate and the crosslinking agent is glutaraldehyde, a catalyst concentration of from about 25 to 35 wt. %, based upon the amount of glutaraldehyde added, can be used. Most preferably, between about 5% and about 30%, based upon the weight of the glutaraldehyde, of an organic acid, such as citric acid, can also be added as a co-catalyst.

The crosslinking solution containing crosslinking agent and catalyst is generally contacted with cellulose fibers for a time period sufficient to saturate the fibers with the crosslinking solution. Preferably, the pH of the aqueous portion of the slurry of cellulose fibers and crosslinking solution is adjusted to a value between about 2 and 5, more preferably between 2.5 and 3.5, during the period of contact between the crosslinking solution and the fibers.

After being contacted with the crosslinking solution, the cellulosic fibers are dewatered and preferably partially dried. Generally, the cellulosic fibers can be dewatered and partially dried to a fiber consistency of between about 30% and about 80% by weight. More preferably, the fibers are dewatered and dried to a consistency level of between about 40% and about 60%. Drying the fibers to within these ranges generally will facilitate defibration of the fibers into individualized form without excessive formation of knots associated with higher moisture levels and without high levels of fiber damage associated with lower moisture levels.

Dewatering may be accomplished, for example, by such methods as mechanical pressing, centrifuging, or air drying the fiber slurry. Additional drying can be carried out by such methods, known in the art as air drying or flash drying, under conditions such that the utilization of high temperatures for an extended period of time is not required. Excessively high fiber temperatures at this stage of the process may result in the premature initiation of crosslinking. Preferably, temperatures in excess of about 160° C. are not maintained for periods of time in excess of 2 to 3 seconds.

After dewatering and, optionally, partial drying, the fibers are separated into substantially individualized form. This may be accomplished by mechanically defibrating the fibers into a low density, individualized, form known as "fluff" prior to reaction of the crosslinking agent within the fibers. Mechanical defibration may be performed by a variety of methods which are known in the art. Mechanical defibration is preferably performed by a method wherein knot formation and fiber damage are minimized. One type of device which has been found to be particularly useful for defibrating the cellulosic fibers is the three stage fluffing device described in U.S. Pat. No. 3,987,968, issued Oct. 26, 1936 to D. R. Moore and O. A. Shields, which patent is incorporated herein by reference. The fluffing device described in U.S. Pat. No. 3,987,968 subjects moist cellulosic pulp fibers to a combination of mechanical impact, mechanical agitation, air agitation and a limited amount of air drying to create a substantially knot-free fluff.

Maintaining the fibers in substantially individual form during drying and subsequent crosslinking allows the fibers to twist during drying and thereby be crosslinked in a twisted, curled state. Drying fibers under such conditions that the fibers may twist and curl is referred to herein as drying the fibers under substantially unrestrained conditions since contact with other fibers inhibits the relative occurrence of twisting and curling of the fiber.

The defibrated fibers can then be heated to a suitable temperature and for a period of time which is effective to cause the crosslinking agent to react within the cellulosic fibers. The rate and degree of crosslinking depend upon the moisture content of the fibers, temperature, amount and type of catalyst and crosslinking agent and the means utilized for heating and/or drying the fibers while crosslinking is performed. Those skilled in the art will recognize that a number of temperature-time relationships exist for the reaction of the crosslinking agent with the fibers. Conventional paper drying temperatures (e.g., 120° C. to about 150° C.), for periods of between about 30 minutes and 60 minutes, under static, atmospheric conditions will generally provide acceptable crosslinking reaction efficiencies for fibers having moisture contents less than about 5%. Those skilled in the art will also appreciate that higher temperatures and increased air flow rates decrease the time required for the crosslinking reaction. However, reaction temperatures are preferably maintained at less than about 160° C., since exposure of the fibers to such high temperatures in excess of about 160° C. may lead to yellowing or other damaging of the fibers.

Following the crosslinking step, the fibers can be washed with a basic substance such as caustic in order to neutralize any acid remaining in the pulp. After washing, the fibers can again be defluidized and dried. The fibers while still in a moist condition may be subjected at this point to a second mechanical defibration step which causes the crosslinked fibers to twist and curl between the defluidizing and drying steps. The same apparatus and methods previously described for defibrating the fibers are applicable to this second mechanical defibration step. As used herein, the term "defibration" refers to any of the procedures which may be used to mechanically separate the fibers into substantially individual form, or to maintain them in this state if the fibers are already in such form. "Defibration", therefore, refers to the step of mechanically treating the fibers, in either individual form or in a more compacted form, wherein such mechanical treatment step (a) separates the fibers into substantially individual form if they are not already in such form, and (b) imparts curl and twist to the fibers upon drying. This second post crosslinking defibration treatment is believed to increase the twisted, curled character of the pulp.

The preferred stiffened, twisted, curled cellulose fibers prepared in the foregoing manner may be subjected to additional treatment steps to reduce residual crosslinker levels, to bleach the fibers or to form the fibers into pulp sheets suitable for subsequent processing into the air-laid structures used in the absorbent articles herein. Processing of these fibers in these various ways is described in greater detail in European Patent Publication No. 256,676, Published Jan. 7, 1988, and European Patent Publication No. 252,650, Published Jan. 13, 1988, both of which were filed in the name of The Buckeye Cellulose Corporation, a wholly-owned subsidiary of The Procter & Gamble Company. These patent applications, which also provide a number of additional details concerning the stiffened, twisted, curled cellulose fibers preferred for use in the present invention, are incorporated herein by reference.

As indicated hereinbefore, the stiffened, twisted, curled cellulose fibers of any of the foregoing types can be combined with particles of polymeric gelling agent to form both the upper and lower layers of the absorbent core of the absorbent articles herein. Like the fiber component of these layers, the particles of polymer gelling agent employed in both layers of the absorbent core must also be of a particular type. These polymeric gelling agents are those materials which, upon contact with fluids (i.e., liquids) such as water or body fluids, imbibe such fluids and thereby form hydrogels. In this manner, fluid discharged into both layers of the absorbent core herein can be acquired and held by the particles of the polymeric gelling agent, thereby providing the articles herein with enhanced absorbent capacity and/or improved fluid retention performance.

The polymeric gelling agent particles which are employed in both layers of the absorbent core will generally comprise a substantially water-insoluble, slightly cross-linked, partially neutralized, hydrogel-forming polymer material. Such polymer materials can be prepared from polymerizable, unsaturated, acid-containing monomers. Suitable unsaturated acidic monomers for use in preparing the polymeric gelling agents used in this invention include those listed in Brandt/Goldman/Inglin; U.S. Pat. No. 4,654,039, issued Mar. 31, 1987, incorporated herein by reference. Preferred monomers include acrylic acid, methacrylic acid, and 2-acrylamido-2-methyl propane sulfonic acid. Acrylic acid itself is especially preferred for preparation of the polymeric gelling agent material.

In the hydrogel-forming polymeric gelling agent the polymeric component formed from unsaturated, acid-containing monomers may be grafted on to other types of polymer moieties such as starch or cellulose. Polyacrylate grafted starch materials of this type are also especially preferred for use herein.

Preferred polymer gelling agents which can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric gelling agents used in both layers of the absorbent cores herein, such materials will in general be slightly cross-linked. Cross-linking serves to render the hydrogel-forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in Masuda et al; U.S. Pat. No. 4,076,663; issued Feb. 28, 1978, incorporated herein by reference. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent can generally comprise from about 0.001 mole percent to 5 mole percent of the resulting hydrogel-forming polymer material. More preferably, the cross-linking agent will comprise from about 0.01 mole percent to mole percent of the hydrogel-forming polymeric gelling agent used herein.

The slightly cross-linked, hydrogel-forming polymeric gelling agents which may be used in the articles of the present invention are generally employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

The polymeric gelling agent materials used in the absorbent articles herein must have a relatively high capacity for imbibing fluids encountered in such articles. The absorbent capacity of these materials can be quantified by referencing the "gel volume" of the polymeric gelling agents which are to be selected for use in the present invention.

For purposes of this invention, gel volume can be defined in terms of the amount of synthetic urine absorbed by any given polymeric gelling agent and is specified as grams of synthetic urine per gram of polymeric gelling agent. Gel volume in synthetic urine can be determined by forming a suspension of about 0.1–0.2 parts of dried polymeric gelling agent to be tested with about 20 parts of synthetic urine. This suspension is maintained at ambient temperature under gentle stirring for a time sufficient, e.g., about 1 hour, for swelling equilibrium to be attained. Using a procedure described in greater detail hereinafter in the Test Methods section, the gel volume of the polymeric gelling agent in grams of synthetic urine per gram of polymeric gelling agent is then calculated from the weight fraction of the polymeric gelling agent in the suspension and the ratio of the liquid volume excluded from the formed hydrogel to the total volume of the suspension.

The gel volume of the gelling agents used in both layers of the absorbent cores herein will generally be at least about 20 grams of synthetic urine per gram of polymeric gelling agent. More preferably, the gel volume of the materials employed will range from about 20 to 60, most preferably from about 22 to 35 grams of synthetic urine per gram of polymeric gelling agent.

Another feature of the polymeric gelling agents which are especially useful in the absorbent articles herein relates to the level of extractable polymer material present in such hydrogel-forming material. Extractable polymer levels can be determined by contacting a sample of hydrogel-forming polymeric gelling agent material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the polymeric gelling agents used herein is also set forth in the hereinbefore referenced U.S. Pat. No. 4,654,039 and in its allowed Reissue application Ser. No. 060,718 now U.S. Pat. Re. No. 32,649. Polymeric gelling agent materials especially useful in the articles herein are those which have an equilibrium extractables content in synthetic urine of no more than about 17%, preferably no more than about 10% by weight of the polymeric gelling agent.

An essential feature of the present invention is the utilization of the above-described polymeric gelling agents in at least the upper layer of the absorbent core in the form of nonfibrous particles having certain particle size characteristics. In particular, it has been discovered that especially thin absorbent articles of especially high absorbent capacity can be realized by incorporating polymeric gelling agent into the particular upper absorbent core layer herein in the form of particles which are generally larger than those which have heretofore been conventionally employed. Generally, provision of gelling agent particles of this relatively larger size requires the use of one or more gelling agent manufacturing or processing techniques which eliminate or reduce the amount of smaller, finer gelling agent particles which are introduced, along with the stiffened, twisted, curled cellulose fibers, into the absorbent articles herein. An upper limit on gelling agent particle size is also provided since gelling agent particles which are too large are less desirable from a consumer aesthetics standpoint.

Specifically, the present invention requires the utilization in at least the upper layer of the core of the absorbent articles herein of polymeric gelling agent particles of a selected mass median particle size. For purposes of the present invention, particle size is defined as the dimension of a gelling agent particle which is determined by sieve size analysis. Thus, for example, in principle, a particle that is retained on a sieve with 710 micron openings is considered to have a particle size greater than 710 microns, a particle that passes through a sieve with 710 micron openings and is retained on a sieve with 500 micron openings is considered to have a particle size between 500 and 710 microns, and a particle that passes through a sieve with 500 micron openings is considered to have a particle size less than 500 microns.

Further, for purposes of this invention, the mass median particle size of a given sample of gelling agent particles is defined as the particle size which divides the sample in half on a mass basis, i.e., half of the sample by weight will have a particle size greater than the mass median particle size and half of the sample by weight will have a particle size less than the mass median particle size. Thus, for example, the mass median particle size of a sample of gelling agent particles is 500 microns if one half of the sample by weight is retained on a sieve with openings of 500 microns. A standard particle-size plotting method (wherein cumulative weight percent of the particle sample retained on or passed through a given sieve size is plotted versus sieve-opening size on probability paper) is typically used to determine mass median particle size when the 50% mass value does not correspond to the size opening of a U.S.A. Standard Testing Sieve. A plot of this type is also typically used to determine the distribution of particle size about the mass median value.

The polymeric gelling agent particles employed in at least the upper core layer of the absorbent articles of this invention must have a mass median particle size within the range of from about 400 to 1680 microns. More preferably, mass median particle size of such particles will range from about 410 to 1190 microns. Most preferably, mass median particle size of the gelling agent particles used in the upper core layer will range from about 420 to 700 microns.

The size of the gelling agent particles used in the lower layer of the absorbent core is not critical and can vary over a wider mass median particle size range than the gelling agent employed in the upper layer (for example, from about 200 to 2,000 microns). Preferably, however, the same size particles as are used in the upper layer will also be employed in the lower layer of the absorbent core.

The gelling agent particles used in the upper layer will also preferably have a certain maximum particle size deviation from the mass median particle size. In particular, it is preferred that no more than about 16% by weight of the gelling agent particles in the upper layer have a particle size less than 200 microns and no more than about 16% by weight of these particles have a particle size greater than 1410 microns. More preferably, no more than about 16% by weight of these particles should have a particle size less than 210 microns and no more than about 16% by weight of these particles should have a particle size greater than 1100 microns. Most preferably, no more than about 16% by weight of the gelling agent particles should have a particle size less than 220 microns and no more than about 16% by weight of the gelling agent particles should have a particle size greater than 900 microns.

The polymeric gelling agent particles useful in the upper layer can be adjusted to, or close to, the requisite particle size distribution by controlling the processing techniques used to prepare the gelling agent. Frequently this will involve varying and monitoring the conditions under which the gelling agent is polymerized, dried, chopped, ground and/or agglomerated. Once gelling agent particles are formed by whatever process, further treatment such as screening may be required to remove particles which, if left in, would cause the gelling agent particle component to fall outside of the hereinbefore-described particle size requirements.

One preferred technique for preparing particles which are larger than those ordinarily prepared by gelling agent polymerization-drying-chopping techniques involves agglomeration of smaller particles to produce larger agglomerates. Agglomeration techniques can thus be used to raise the mass median particle size of gelling agent particles and to thereby provide particles in agglomerated form which are suitable for use in the articles herein. Agglomeration techniques are well known in the art and may or may not involve the use of moisture addition to smaller gelling agent particles or the use of a binder or other type of agglomerating medium.

Gelling agent particles used in the absorbent articles herein, and especially those in agglomerated form, will generally be nonfragile. Nonfragile particles are those which are stable enough to withstand the forces encountered during conventional absorbent article manufacture and/or use without breaking apart and separating into their smaller component particles.

Both the upper and lower layers of the absorbent core, with their stiffened, twisted, curled cellulose fibers and the polymeric gelling agent particles as hereinbefore described, can be prepared by any process or technique which provides a web comprising a combination of the fibers and the gelling agent particles. Within such a fiber/particle combination, the gelling agent particles should be thoroughly dispersed among the stiffened, twisted, curled cellulose fibers forming the web. For purposes of this invention, gelling agent particles are "thoroughly dispersed" among the cellulosic fibers if there are no significant instances of individual gelling agent particles being in contact only with each other and not with one or more of the fibers. Preferably, this will mean that there should be no zones or regions (e.g., zones or regions of 2, more preferably 1, cubic centimeters or larger) within either layer of the absorbent core wherein the concentration of gelling agent exceeds the upper limits set forth hereinbefore for gelling agent concentration in each layer.

Within the webs which form the layers of the absorbent core, the particles of the polymeric gelling agent must be thoroughly dispersed but may or may not be uniformly distributed. In particular, there may be regions or zones of the core layers which have higher concentrations of gelling agent particles than do other regions or zones of the layers. In one embodiment of this type, there may be a concentration gradient of gelling agent particles along the thickness dimension of one or both layers with the lowest concentration of gelling agent being at or near the surface of the layer which receives fluid and the highest concentration of gelling agent being at or near the opposite end of the thickness dimension.

Both the upper and lower layers of the absorbent core can be formed by air-laying a substantially dry mixture of stiffened, twisted, curled cellulose fibers and polymeric gelling agent particles and, if desired or necessary, densifying the resulting web. Such a procedure is in general described more fully in the hereinbefore referenced Weisman and Goldman; U.S. Pat. No. 4,610,678; issued Sept. 9, 1986.

As indicated in U.S. Pat. No. 4,610,678, the air-laid webs formed by this procedure will preferably comprise substantially unbonded fibers and will preferably have a moisture content of 10% or less. In preparing webs of this invention by an airlaying process or by any other conventional procedure, care should be taken in handling and transporting the polymeric gelling agent particles so as to avoid breaking these particles down into smaller particles. This is especially true when the gelling agent particles are in an agglomerated form wherein the agglomerates may be more fragile than nonagglomerated particles. If the gelling agent particles, e.g., agglomerates, are roughly treated during web structure preparation or thereafter, the particles actually incorporated into the upper layer of the absorbent core may not have the requisite particle size distribution characteristics set forth hereinbefore.

It has been discovered that the gelling agent-containing lower fluid storage layer of the absorbent core need not be as large as the upper fluid acquisition/distribution layer of the core and can, in fact, have a top surface area (in the unfolded configuration) which is substantially smaller than the top surface area (unfolded) of the upper layer of the absorbent core. Generally, the top surface area of the lower fluid storage layer will range from 0.25 to 0.95 times that of the upper acquisition/distribution layer. More preferably the top surface area of the lower layer will be only from about 0.25 to 0.75, and most preferably from about 0.3 to 0.5, times that of the upper layer.

In accordance with the present invention, the lower fluid storage layer of the absorbent core should be placed in a specific positional relationship with respect to the backing sheet and/or the upper fluid acquisition/distribution layer in the absorbent article. More particularly, the gelling agent-containing lower fluid storage layer of the core must be positioned generally toward the front of the absorbent article so that gelling agent is most effectively located to drain and hold discharged body fluid from the upper acquisition/distribution layer. For purposes of the present invention, the front of the absorbent articles herein means the end of the absorbent article which is intended to be placed on the front of the wearer. Thus the lower fluid storage layer is to be placed in the vicinity of the point of discharge of body fluids.

The generally forward positioning of the lower gelling agent-containing fluid storage layer can be defined by specifying the percentage of total lower layer gelling agent which is found forward of particular points along the length of the absorbent article. Thus, in accordance with the present invention, the lower gelling agent-containing fluid storage layer is positioned relative to the upper elongated backing sheet and/or the acquisition/distribution layer such that (1) at least about 75% of the total gelling agent in the lower fluid storage layer is found within the front two-thirds section of the absorbent article, and (2) at least about 55% of the total gelling agent in the lower fluid storage layer is found within the front half section of the absorbent article.

More preferably, the lower fluid storage layer of the core is positioned relative to the elongated backing sheet and/or the upper acquisition/distribution layer such that at least about 90% of the total gelling agent in the lower layer is found in the front two-thirds section and at least about 60% of the total gelling agent in the lower layer is found in the front half section of the absorbent article. As noted, for purposes of the present invention, "sections" of the absorbent article can be defined by reference to top surface areas of the unfolded absorbent article found in front of a given point on the line which defines the length of the absorbent article.

For purposes of determining such lower layer positioning, the length of the absorbent article will be taken as the normal longest longitudinal dimension of the elongated article backing sheet. This normal longest dimension of the elongated backing sheet can be defined with respect to the article as it is applied to the wearer. When worn, the opposing ends of the backing sheet are fastened together so that these joined ends form a circle around the wearer's waist. The normal length of the backing sheet will thus be the length of the line running through the backing sheet from (a) the point on the edge of the backing sheet at the middle of the wearer's back waist, through the crotch, to (b) the point on the opposite edge of the backing sheet at the middle of the wearer's front waist.

In the usual instance wherein the upper layer of the absorbent core generally defines the shape of the absorbent article, the normal length of the elongated article backing sheet will be approached by the longest longitudinal dimension of the upper layer of the core. In such instances the positioning of the gelling agent-containing lower fluid storage layer can also be defined with respect to its location toward the front portion of the elongated upper fluid acquisition/distribution layer. However, in some applications (e.g. adult incontinence articles) wherein bulk reduction or minimum cost are important, the upper fluid acquisition/distribution layer would not take on the general shape of the diaper or incontinence structure. Rather the upper layer would be generally located to cover only the genital region of the wearer and could in this case have approximately the same top surface area as the lower fluid storage layer. In this instance both the upper fluid acquisition/distribution layer and the co-extensive lower fluid storage layer would be located toward the front of the article as defined by the backing sheet such that the requisite percentages of lower layer gelling agent would be found in the front two-thirds and front half sections respectively of the article.

The lower fluid storage layer of the absorbent core can be of any desired shape consistent with comfortable fit including, for example, circular, rectangular, trapezoidal or oblong, e.g., hourglass-shaped, dog-bone-shaped, half dog bone shaped, oval or irregularly shaped. This lower fluid storage layer need not be physically separated from the upper fluid acquisition/distribution layer and can simply form a zone of high gelling agent concentration in a continuous web of stiffened, twisted, curled cellulose fiber material. More preferably, however, the lower fluid storage layer of the absorbent core will comprise a separate web which can be used as an insert placed underneath a larger elongated upper acquisition/distribution layer. If desired, such an insert can be wrapped in a high wet strength envelope web such as tissue paper or a synthetic fine pore, e.g., nonwoven, material, to minimize the potential for gelling agent particles to migrate out of the insert layer. Another objective of such overwrapping is to desirably increase the in-use integrity of the dual layer core. Such a web can, in fact, be glued to the lower fluid storage insert layer. Suitable means for carrying out this gluing operation include the glue spraying procedure described in Minetola and Tucker; U.S. Pat. No. 4,573,986, issued Mar. 4, 1986, incorporated herein by reference.

In preferred embodiments, the lower fluid storage layer of the absorbent core will be assymetrically oblong. In especially preferred embodiments, an oblong insert overwrapped with spray-glued tissue will be employed.

Figure 1:
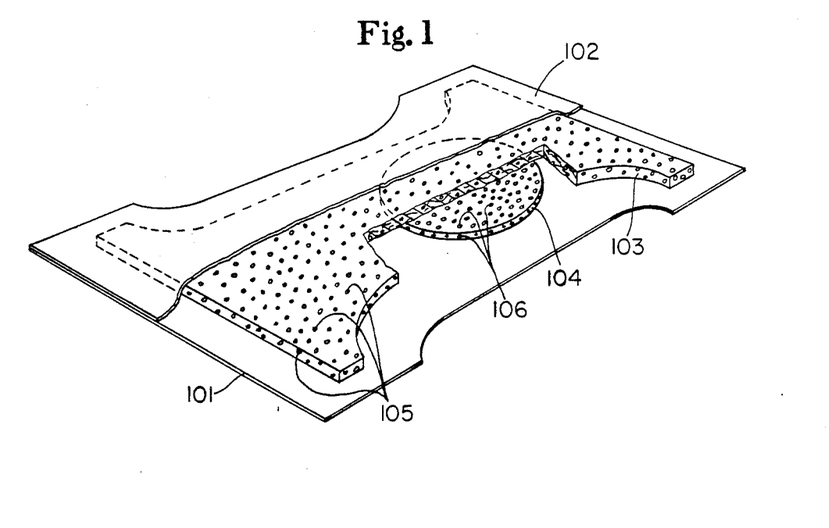
FIG. 1 represents a cutaway view of a diaper structure having the dual-layer absorbent core configuration of the present invention.

One embodiment of an absorbent article according to the present invention comprises a disposable diaper such as that shown in FIG. 1 of the drawing. FIG. 1 shows an hourglass-shaped diaper structure comprising a liquid impervious elongated backing sheet 101 and a water pervious topsheet 102. The absorbent core of the structure comprises two separate layers, i.e., an upper, hourglass-shaped, fluid acquisition/distribution layer 103 and a smaller, lower, oval insert fluid storage layer 104. The upper layer 103 comprises a web of air-laid stiffened, twisted, curled cellulose fibers and discrete, relatively large particles 105 of polymeric gelling agent distributed throughout this upper hourglass-shaped layer. The lower oval insert layer 104 also comprises a web of stiffened, twisted, curled cellulose fibers and also contains discrete particles 106 of polymeric gelling agent distributed throughout this lower oval insert layer. The lower oval insert layer 104 is positioned beneath the upper layer 103 toward the front of the diaper. In this manner at least 90% of the gelling agent material 106 in the lower insert layer 104 is found underneath the front two-thirds section of the upper layer 103 and at least 60% of this gelling agent material 106 is found underneath the front half section of the upper layer 103.

TEST METHODS

In describing the present invention herein, certain characteristics of the stiffened, twisted, curled cellulose fibers and the polymeric gelling agent are set forth. Where reported, these characteristics can be determined using the following test methods:

Twist Count Image Analysis Method

This method is used to determine the twist count of the stiffened, twisted, curled cellulose fibers used in the absorbent articles of the present invention.

Dry fibers are placed on a slide coated with a thin film of immersion oil, and then covered with a cover slip. The effect of the immersion oil is to render the fiber transparent without inducing swelling. This aids in identification of the twist nodes (described hereinafter). Wet fibers are placed on a slide by pouring a low consistency slurry of the fibers on the slide which is then covered with a cover slip. The water renders the fibers transparent so that twist node identification is facilitated.

An image analyzer comprising a computer-controlled microscope, a video camera, a video screen, and a computer loaded with QUIPS software, available from Cambridge Instruments Limited (Cambridge, England; Buffalo, N.Y.), is used to determine twist count.

The total length of fibers within a particular area of the microscope slide at 200× magnification is measured by the image analyzer. The twist nodes are identified and marked by an operator. This procedure is continued, measuring fiber length and marking twist nodes until five inches of total fiber length are analyzed. The number of twist nodes per millimeter is calculated from this data by dividing the total fiber length into the total number of twist nodes marked.

Curl Factor Image Analysis Method

This method is utilized to measure the fiber curl factor of the stiffened, twisted, curled cellulose fibers used in the present invention.

Figure 2:
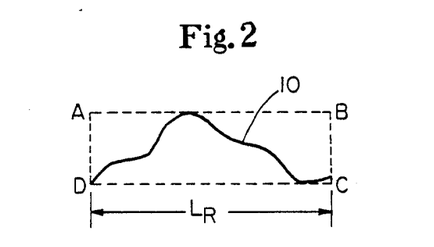
FIG. 2 illustrates the parameter of projected fiber length, $L_R$, used to calculate a curl factor for the stiffened, twisted, curled cellulose fibers used herein.

Dry fibers are placed onto a microscope slide. A cover slip is placed over the fibers and glued in place at the edges. The actual length $L_A$ and the maximum projected length $L_R$ (equivalent to the length of the longest side of a rectangle encompassing the fiber) are measured utilizing an image analyzer comprising a software controlled microscope, video camera, video monitor, and computer. The software utilized is the same as that described hereinbefore for the Twist Count Image Analysis Method. FIG. 2 shows a curled fiber 10 encompassed by rectangle A—B—C—D having a maximum projected length $L_R$.

Once $L_A$ and $L_R$ are obtained, the curl factor for each individual fiber is calculated according to the following equation:

$$\text{Curl Factor} = (L_A/L_R) - 1$$

The curl factor for each sample of fiber is calculated for at least 250 individual fibers and then averaged to determine the average curl factor for the sample. Fibers having $L_A$ less than 0.25 mm are excluded from the calculation.

Water and Alcohol Retention Values

This procedure is utilized to determine either the water or alcohol retention value (WRV or ARV) of the stiffened, twisted, curled cellulose fibers used in the present invention. For water retention values, the test fluid used is water; for alcohol retention values, the test fluid used is isopropyl alcohol.

A sample of about 0.3 g to about 0.4 g of fibers is soaked in a covered container with about 100 ml of test fluid at room temperature for between about 15 and 20 hours. The soaked fibers are collected on a filter and transferred to an 80-mesh wire basket supported about 1.5 inches above a 60-mesh screened bottom of a centrifuge tube. The tube is covered with a plastic cover, and the sample is centrifuged at a relative centrifuge force of 1,500 to 1,700 gravities for 19 to 21 minutes. The centrifuged fibers are then removed from the basket and weighed. The weighed fibers are dried to a constant weight at 105° C. and reweighed. The water or alcohol retention value is calculated as follows:

$$WRV \text{ or } ARV = \frac{(W - D)}{D} \times 100$$

where,
W = wet weight of the centrifuged fibers;
D = dry weight of the fibers; and
W − D = weight of absorbed test fluid.

Gel Volume of the Gelling Agent

This method is used to determine the gel volume of the polymeric gelling agent particles employed in the absorbent articles of the present invention. Gel volume in terms of grams of synthetic urine absorbed per gram of polymeric gelling agent is determined by swelling the polymer samples in several aliquots of synthetic urine. The amount of such synthetic urine actually absorbed by the polymeric gelling agent is determined by a procedure which involves use of a synthetic urine solution containing Blue Dextran so that optical absorbance measurements can be used to calculate the amount of synthetic urine that is not taken up by the hydrogel which forms.

(a) Blue Dextran Solution Preparation

A 0.03% Blue Dextran (BD) solution is prepared by dissolving 0.3 parts of Blue Dextran (Sigma D-5751) in 1000 parts of Synthetic Urine (SU) solution. Synthetic Urine is 15.0 parts of 1% TRITON X-100, 60.0 parts of NaCl, 1.8 parts of $CaCl_2 \cdot 2H_2O$, and 3.6 parts of $MgCl_2 \cdot 6H_2O$, diluted to 6000 parts with distilled $H_2O$. The resulting solution has an absorbance of about 0.25 at its absorbance maximum of 617 nm.

(b) Hydrogel Equilibration

Aliquots of the hydrogel-forming polymeric gelling agent to be tested are swelled in (i) 20 parts of Synthetic Urine (SU) solution and (ii) 20 parts of Blue Dextran (BD) solution. The suspension in the Blue Dextran (BD) solution is prepared in duplicate. For most hydrogels, 0.1–0.25 parts of hydrogel-forming dried powder is required to give a sufficiently high spectrophotometer reading relative to the Blue Dextran reference solution. One hour of equilibration at ambient temperature under gentle stir-bar stirring is usually sufficient for swelling equilibrium to be attained. After equilibration, a 3 ml aliquot of supernatant is separated from each gel suspension by decantation followed by centrifugation.

(c) Gel Volume Determination

The optical absorbency (ABS) of each supernatant is determined spectrophotometrically with an accuracy of 0.001 absorbance units. The Synthetic Urine solution is used as an ABS = 0.0 reference. The absorbency of the supernatant from the synthetic urine suspension without Blue Dextran should not exceed 0.01 A; higher values indicate scattering from residual hydrogel gel particles or residual additives, and further centrifugation is necessary. The absorbency of the Blue Dextran supernatants should exceed the absorbency of the Blue Dextran reference solution by at least 0.1 absorbance units. Absorbency values below this range indicate the need to adjust the amount of polymeric gelling agent used to prepare the gel suspension.

(d) Gel Volume Calculation

The Gel Volume in synthetic urine of the polymeric gelling agent in gms/gm is calculated from (i) the weight fraction of the polymeric gelling agent in the gel suspension and (ii) the ratio of the excluded volume to the total volume of the suspension. Since Blue Dextran is excluded from the hydrogel due to its high molecular weight, this ratio is related to the measured absorbencies. The following equation is used to calculate the gel volume:

$$\text{Gel Volume} = \left[ \frac{(\text{gms } BD \text{ Solution})}{(\text{gms polymeric gelling agent*})} \right] \times$$

$$\left[ 1 - \frac{(ABS\ BD\ \text{solution})}{(ABS\ BD\ \text{supernatant} - ABS\ SU\ \text{supernatant})} \right]$$

*Corrected to a dry weight basis

Absorbent articles of the present invention in the form of a disposable diaper, as well as their effectiveness at absorbing body fluid, are illustrated by the following examples:

EXAMPLE I

A disposable diaper is prepared comprising a thermally bonded polypropylene topsheet, a fluid impervious polyethylene backing sheet and a dual layer absorbent core positioned between the topsheet and the backing sheet. The dual layer absorbent core comprises an hourglass-shaped primary core positioned below the topsheet and an irregularly-shaped insert layer positioned underneath the hourglass-shaped primary core.

The hourglass primary core comprises a major amount of stiffened, twisted, curled cellulose fibers and a minor amount of particles of a crosslinked sodium polyacrylate gelling agent having a gel volume of about 30 g of synthetic urine per gram of gelling agent and a degree of neutralization of about 70%.

The insert layer comprises an air-laid mixture of stiffened, twisted, curled cellulose fibers and particles of the same sodium polyacrylate gelling agent used in the hourglass layer but present in a concentration significantly higher than in the hourglass core. The insert is positioned toward the front of the hourglass such that 90% of the gelling agent material in the insert layer is found within the front two-thirds section of the disposable diaper and such that about 60% of the gelling agent in the insert is in the front half of the disposable diaper.

The stiffened, twisted, curled cellulose fiber material used in both layers of the absorbent core is similar to the fibers having the characteristics described in Table 1.

TABLE 1

Stiffened, Twisted, Curled Cellulose (STCC) Fibers

Type = Southern softwood kraft pulp crosslinked with glutaraldehyde to the extent of 1.41 mole percent on a dry fiber cellulose anhydroglucose basis
Twist Count Dry = 6.8 nodes/mm
Twist Count Wet = 5.1 nodes/mm
Isopropanol Retention Value = 24%
Water Retention Value = 37%
Curl Factor = 0.63

The particles of sodium polyacrylate gelling agent used in both layers of the absorbent core are sieved such that substantially all of these particles are retained on a 45 mesh (355 micron opening) sieve. Such particles have a mass median particle size of about 490 microns.

Other features of the two layers of the absorbent core are set forth in Table 2.

TABLE 2

| Hourglass: | |
|---|---|
| Density | 0.085 g/cm$^3$ |
| Basis Weight | 0.015 g/cm$^2$ |
| Area | 607 cm$^2$ |
| % Gelling Agent | 6.5% by weight of hourglass |
| Insert | |
| Density | 0.168 g/cm$^3$ |
| Basis Weight | 0.063 g/cm$^2$ |
| Area | 260 cm$^2$ |
| % Gelling Agent | 30% by weight of insert |
| Overall Gelling Agent Content: | 20% by weight of total core |

A diaper having this configuration has exceptionally high absorbent efficiency, and the relatively high density of the core layers permits construction of especially thin diaper products.

EXAMPLE II

The leakage performance of a diaper of the EXAMPLE I type is compared with that of a dual layer core control diaper similar in configuration to the diapers commercially marketed under the tradename ULTRA PAMPERS PLUS. The control diaper utilizes conventional air laid wood pulp fibers (Foley fluff) in both layers of the absorbent core. Furthermore, the control diaper utilizes polymeric gelling agent in only the lower insert layer of the core and uses it in the form of particles which are generally smaller than those employed in the absorbent articles of the present invention. The assymetrical lower insert layer of the core of the control diaper also has a low density zone (LDZ), i.e., a region of generally lower density than in the rest of the hourglass layer, positioned toward the front of the insert layer to enhance fluid acquisition and distribution performance of the lower insert layer.

A detailed description of the two products tested is set forth in Table 3.

TABLE 3

| Product Description | Example I Type Diaper | Control Diaper |
|---|---|---|
| General | | |
| Core Type | Dual Layer | Dual Layer with LDZ |
| Fiber Type | STCC* | Foley Fluff |
| Polymeric Gelling Agent (PGA) Type | Na Polyacrylate with gel volume = ~30 g/g | Na Polyacrylate agglomerates with gel volume = ~30 g/g |
| PGA Mass Median Particle Size (microns) | ~490 | ~350–400 |
| Stack Height** (inches) | 3.0 | 5.0 |
| Hourglass Layer (Target Values) | | |
| Fiber Weight, g | 10.02 | 16.04 |
| PGA Weight, g | 0.70 | 0.00 |
| PGA % | 6.5 | 0.0 |
| Total Hourglass Wt., g | 10.72 | 16.04 |
| Insert Layer (Target Values) | | |
| Fiber Weight, g | 10.98 | 11.63 |
| PGA Weight, g | 4.70 | 5.50 |
| PGA % | 30.0 | 32.1 |
| Total Insert Weight, g | 15.68 | 17.13 |
| Total Core (Target Values) | | |
| Fiber Weight, g | 21.00 | 27.67 |

TABLE 3-continued

| Product Description | Example I Type Diaper | Control Diaper |
|---|---|---|
| PGA Weight, g | 5.40 | 5.50 |
| Total Core Weight, g | 26.40 | 33.17 |

*STCC = Stiffened, twisted, curled cellulose of the type described in Example I.
**Stack Height refers to the height of a stack of 10 diapers under an 850 g weight and is a measure of the compactness of the diapers in the stack.

Diapers of the types described in Table 3 are tested for leakage using a test panel of 50 babies, evenly split by sex, who use the products around the clock. Caregivers of the panel babies are given 18 diapers of each type (3 days' worth) and are asked to keep diary records are then used changes during this period. These diary records are then used to calculate the percent of diapers used which leak and the amount of urine held by each diaper. Diaper changes with urine only are used in such calculations.

Detailed tabulations showing leakage experience in such a diary study, broken down by daytime, nap time and overnight usage and by baby sex are shown in Table 4.

| Leakage Experience | All Babies | | Male Babies | | Female Babies | |
|---|---|---|---|---|---|---|
| | Ex. I | Control | Ex. I | Control | Ex. I | Control |
| Overall | | | | | | |
| # Changes | 558 | 504 | 264 | 244 | 294 | 260 |
| % Leakage | 5.4 | -S- 8.3 | 5.7 | 9.4 | 5.1 | 7.3 |
| Daytime | | | | | | |
| # Changes | 269 | 256 | 118 | 123 | 151 | 128 |
| % Leakage | 0.4 | 2.7 | 0.8 | 1.6 | 0.0 | 3.8 |
| Nap time | | | | | | |
| # Changes | 128 | 114 | 73 | 54 | 55 | 60 |
| % Leakage | 4.7 | 8.8 | 1.4 | 9.3 | 9.1 | 8.3 |
| Overnight | | | | | | |
| # Changes | 161 | 134 | 73 | 67 | 88 | 67 |
| % Leakage | 14.3 | 18.7 | 17.8 | 23.9 | 11.4 | 13.4 |
| Urine Loading | | | | | | |
| (Basis: Average net weight gain for diaper changes with urine only) | | | | | | |
| Overall | | | | | | |
| Loading, g -nonleaking | 116.9 | 116.7 | 116.3 | 115.7 | 117.4 | 117.8 |
| diapers, g -leaking | 108.8 | 104.4 | 107.4 | 103.6 | 110.0 | 105.1 |
| diapers, g Daytime | 227.3 | 239.7 | 233.6 | 219.0 | 221.3 | 265.3 |
| Loading, g Nap time | 90.2 | 90.5 | 89.8 | 86.0 | 90.5 | 94.7 |
| Loading, g Overnight | 117.1 | 114.0 | 114.8 | 112.0 | 120.1 | 115.9 |
| Loading, g | 161.3 | 170.2 | 160.3 | 173.6 | 162.2 | 166.7 |

Note: -S- indicates difference is significant at 90% confidence level.

The Table 4 data indicate that a diaper of the present invention provides overall significantly lower leakage incidence than does a similar dual layer core diaper of the type currently commercially marketed. This is so even though the diaper of the present invention is thinner than the commerical product and employs less material in its absorbent core than the commercial product.

What is claimed is:

1. A disposable absorbent article comprising:
(A) a liquid impervious, elongated backing sheet;
(B) a liquid pervious topsheet; and
(C) a layered absorbent core positioned between said backing sheet and said topsheet, said core comprising:
  (i) an upper fluid acquisition/distribution layer having a density of from about 0.05 to 0.25 g/cm³ and a basis weight of from about 0.01 to 0.10 g/cm² and comprising a combination of stiffened, twisted, curled cellulose fibers, and from about 3% to 15% by weight of said upper layer of particles of a hydrogel-forming polymeric gelling agent thoroughly dispersed among said fibers; and
  (ii) a lower fluid storage layer having a density of from about 0.06 to 0.3 g/cm³ and a basis weight of from about 0.02 to 0.12 g/cm² and comprising a combination of stiffened, twisted, curled cellulose fibers and from about 15% to 60% by weight of said lower layer of particles of a hydrogel-forming polymer gelling agent thoroughly dispersed among said fibers;
wherein in both upper and lower layers the hydrogel-forming polymeric gelling agent has an equilibrium gel volume of at least about 20 grams of synthetic urine per gram of gelling agent and wherein in the upper layer the gelling agent particles have a mass median particle size ranging from about 400 to 1680 microns;

said lower fluid storage layer having a top surface area which is from about 0.25 to 0.95 times that of said upper fluid acquisition/distribution layer and said lower fluid storage layer further being positioned relative to said backing sheet and said upper layer in a manner such that at least about 75% of the polymeric gelling agent in said lower layer is found within the front two-thirds section of said absorbent article and such that at least about 55% of the polymeric gelling agent in said lower layer is found within the front half section of said absorbent article.

2. An absorbent article according to claim 1 wherein in both layers of the absorbent core the stiffened, twisted, curled cellulose fibers have
(A) an average dry fiber twist count of at least 4.5 twist nodes per millimeter;
(B) an average wet fiber twist count of at least about 3.0 twist nodes per millimeter and which is at least about 0.5 twist nodes per millimeter less than the average dry fiber twist count;
(C) a curl factor of at least about 0.30;
(D) a water retention value of from about 28% to 50%; and
(E) an alcohol retention value of less than about 30%.

3. An absorbent article according to claim 2 wherein
(A) the upper fluid acquisition/distribution layer is elongated, has a density which ranges from about 0.07 to 0.14 g/cm³ and a basis weight which ranges from about 0.07 to 0.12 g/cm²;
(B) the lower fluid storage layer has a density which ranges from about 0.09 to 0.25 g/cm³ and a basis weight which ranges from about 0.04 to 0.08 g/cm²;
(C) the lower fluid storage layer has a top surface area which is from about 0.25 to 0.75 times that of said upper layer; and
(D) at least about 90% of the gelling agent material in said lower fluid storage layer is found in the front two-thirds section of the absorbent article and at least about 60% of the gelling agent material in the lower fluid storage layer is found in the front half section of the absorbent article.

4. An absorbent article according to claim 3 wherein the gelling agent is a substantially water-insoluble, slightly crosslinked, partially neutralized polymer selected from hydrolyzed acrylonitrile grafted starch, polyacrylate grafted starch, polyacrylates, maleic anhydride-based copolymers and combinations of these polymers.

5. An absorbent article according to claim 4 in the form of a diaper wherein:
(A) the topsheet is coextensive with one face of the absorbent core; and
(B) the backing sheet is coextensive with the face of the absorbent core opposite the face covered by the topsheet and has a width greater than that of the core, to thereby provide side marginal portions of the backing sheet which extend beyond the core.

6. An absorbent article according to claim 5 wherein the lower fluid storage layer is a separate insert layer which is overwrapped with a high wet strength envelope web.

7. An absorbent article according to claim 6 wherein the envelope web is tissue and is glue-sprayed to the lower fluid storage insert layer.

8. A disposable absorbent article comprising:
(A) a liquid impervious, elongated backing sheet;
(B) a liquid pervious topsheet; and
(C) a layered absorbent core positioned between said backing sheet and said topsheet, said core comprising:
  (i) an upper fluid acquisition/distribution layer having a density of from about 0.05 to 0.25 g/cm$^3$ and a basis weight of from about 0.01 to 0.10 g/cm$^2$ and consisting essentially of an airlaid mixture of stiffened, twisted curled cellulose fibers; and from about 3% to 15% by weight of said upper layer of particles of a hydrogel-forming polymeric gelling agent; and
  (ii) a lower fluid storage layer having a density of from about 0.06 to 0.3 g/cm$^3$ and a basis weight of from about 0.02 to 0.12 g/cm$^2$ and consisting essentially of an airlaid mixture of stiffened curled cellulose fibers and from about 15% to 60% by weight of said lower layer of particles of a hydrogel-forming polymer gelling agent;
  wherein, in both upper and lower layers;
    (a) the stiffened, twisted, curled cellulose fibers have an average dry fiber twist count of at least about 4.5 twist nodes per millimeter, an average wet fiber twist count of at least about 3.0 twist nodes per millimeter and which is at least about 0.5 twist nodes per millimeter less than the average dry fiber twist count, a curl factor of at least about 0.30, a water retention value between about 28% and 50% and an alcohol retention value of less than about 30%; and
    (b) the hydrogel-forming polymeric gelling agent has an equilibrium gel volume of at least about 20 grams of synthetic urine per gram of gelling agent and the gelling agent particles have a mass median particle size ranging from about 410 to 1190 microns with no more than about 16% by weight of said particles having a particle size less than 200 microns and no more than about 16% by weight of said particles having a particle size greater than 1410 microns;
    said lower fluid storage layer having a top surface area which is from about 0.25 to 0.95 times that of said upper fluid acquisition/distribution layer and said lower fluid storage layer further being positioned relative to said backing sheet and said upper layer in a manner such that at least about 75% of the polymeric gelling agent in said lower layer is found within the front two-thirds section of said absorbent article and such that at least about 55% of the polymeric gelling agent in said lower layer is found within the front half section of said absorbent article.

9. An absorbent article according to claim 8 wherein in both layers of the absorbent core the stiffened, twisted, curled cellulose fibers have
(A) an average dry fiber twist count of at least about 5.5 twist nodes per millimeter;
(B) an average wet fiber twist count of at least about 4.0 twist nodes per millimeter and which is at least about 1.0 twist nodes per millimeter less than the average dry fiber twist count;
(C) a curl factor of at least about 0.50;
(D) a water retention value of from about 30% to 45%; and
(E) an alcohol retention value of less than about 27%.

10. An absorbent article according to claim 9 wherein
(A) the upper fluid acquisition/distribution layer is elongated, has a density which ranges from about 0.07 to 0.14 g/cm$^3$ and a basis weight which ranges from about 0.01 to 0.025 g/cm$^2$;
(B) the lower fluid storage layer has a density which ranges from about 0.09 to 0.25 g/cm$^3$ and a basis weight which ranges from about 0.04 to 0.08 g/cm$^2$;
(C) the lower fluid storage layer has a top surface area which is from about 0.25 to 0.75 times that of said upper layer; and
(D) at least about 90% of the gelling agent material in said lower fluid storage layer is found in the front two-thirds section of the absorbent article and at least about 60% of the gelling agent material in the lower fluid storage layer is found in the front half section of the absorbent article.

11. An absorbent article according to claim 10 wherein the gelling agent is a substantially water-insoluble, slightly crosslinked, partially neutralized polymer selected from hydrolyzed acrylonitrile grafted starch, polyacrylate grafted starch, polyacrylates, maleic anhydride-based copolymers and combinations of these polymers.

12. An absorbent article according to claim 11 in the form of a diaper wherein:
(A) the topsheet is coextensive with one face of the absorbent core; and
(B) the backing sheet is coextensive with the face of the absorbent core opposite the face covered by the topsheet and has a width greater than that of the core, to thereby provide side marginal portions of the backing sheet which extend beyond the core.

13. An absorbent article according to claim 12 wherein the lower fluid storage layer is a separate insert layer which is overwrapped with a high wet strength envelope web.

14. An absorbent article according to claim 13 wherein the envelope web is tissue and is glue-sprayed to the lower fluid storage insert layer.

15. A disposable absorbent article comprising:
(A) a liquid pervious, elongated backing sheet;
(B) a liquid pervious topsheet; and
(C) a layered absorbent core positioned between said backing sheet and said topsheet, said core comprising:
  (i) an hourglass-shaped upper fluid acquisition/distribution layer having a density of from about 0.07 to 0.12 g/cm$^3$ and a basis weight of from about 0.013 to 0.020 g/cm$^2$ and consisting essentially of an airlaid mixture of stiffened, twisted, curled cellulose fibers; and from about 5% to 8% by weight of said upper layer of particles of a hydrogel-forming polyacrylate or polyacrylate grafted starch gelling agent; and (ii) a lower fluid storage layer having a density of from about 0.15 to 0.20 g/cm$^3$ and a basis weight of from about 0.05 to 0.07 g/cm$^2$ and consisting essentially of an airlaid mixture of stiffened curled cellulose fibers and from about 20% to 50% by weight of said lower layer of particles of a hydrogel-forming polyacrylate or polyacrylate grafted starch gelling agent;

wherein in both upper and lower layers
(a) the stiffened, twisted, curled cellulose fibers have an average dry fiber twist count of at least about 6.5 twist nodes per millimeter, an average wet fiber twist count of at least about 5.0 twist nodes per millimeter and which is at least 1.0 twist nodes per millimeter less than the average dry fiber twist count, a curl factor of at least about 0.5, a water retention value of from about 35% to 42% and an alcohol retention value of less than about 27%; and
(b) the hydrogel-forming gelling agent has an equilibrium gel volume of from about 22 to 35 grams of synthetic urine per gram of gelling agent and the gelling agent particles have a mass median particle size ranging from about 410 to 1190 microns with no more than about 16% by weight of said particles having a particle size less than 210 microns and no more than about 16% by weight of said particles having a particle size greater than 1100 microns;

said lower fluid storage layer having a top surface area which is from about 0.25 to 0.75 times that of said upper fluid acquisition/distribution layer and said lower fluid storage layer further being positioned relative to said backing sheet and said upper layer in a manner such that at least about 90% of the gelling agent in said lower layer is found within the front two-thirds section of said absorbent article and such that at least about 60% of the gelling agent in said lower layer is found within the front half section of said absorbent article.

16. An absorbent article according to claim 15 wherein the stiffened, twisted, curled cellulose fibers in both layers are crosslinked with a $C_2$-$C_8$ dialdehyde.

17. An absorbent article according to claim 16 wherein the polyacrylate or polyacrylate grafted starch gelling agent has an equilibrium extractable polymer content in synthetic urine of no more than about 17% by weight and wherein the particles of said gelling agent in both layers have a mass median particle size of from about 420 to 700 microns.

18. An absorbent article according to claim 17 in the form of a diaper wherein:
(A) the topsheet is coextensive with one face of the absorbent core; and
(B) the backing sheet is coextensive with the face of the absorbent core opposite the face covered by the topsheet and has a width greater than that of the core, to thereby provide side marginal portions of the backing sheet which extend beyond the core.

19. An absorbent article according to claim 18 wherein the lower fluid storage layer is a separate insert layer which is overwrapped with a high wet strength envelope web.

20. An absorbent article according to claim 19 wherein the envelope web is tissue and is glue-sprayed to the lower fluid storage insert layer.

* * * * *